United States Patent [19]
Beitz et al.

[11] Patent Number: 5,972,685
[45] Date of Patent: Oct. 26, 1999

[54] ORAL ADMINISTRATION OF COPROSTANOL PRODUCING MICROORGANISMS TO HUMANS TO DECREASE PLASMA CHOLESTEROL CONCENTRATION

[75] Inventors: Donald C. Beitz; Jerry W. Young, both of Ames, Iowa; Ling Li, Birmingham, Ala.; Kimberly K. Buhman, West Lafayette, Ind.

[73] Assignee: Iowa State University Research Foundation, Inc., Ames, Iowa

[21] Appl. No.: 08/511,397

[22] Filed: Aug. 4, 1995

Related U.S. Application Data

[63] Continuation of application No. 07/970,565, Nov. 3, 1992, abandoned, and a continuation-in-part of application No. 07/796,403, Nov. 22, 1991, Pat. No. 5,436,004, which is a continuation-in-part of application No. 07/339,229, Apr. 17, 1989, abandoned, which is a continuation-in-part of application No. 07/222,016, Jul. 21, 1988, Pat. No. 4,921,710.

[51] Int. Cl.$^6$ ..................................................... C12N 1/12
[52] U.S. Cl. ..................... 435/252.1; 435/189; 424/93.4; 424/94.4; 424/463; 424/490
[58] Field of Search ................... 424/94.3, 94.4, 424/93.4, 195.1, 490, 491, 488, 463; 435/189, 220, 252.1; 426/56, 42

[56] References Cited

U.S. PATENT DOCUMENTS

| | | | |
|---|---|---|---|
| Re. 30,910 | 4/1982 | Weigand | 424/238 |
| 2,697,106 | 12/1954 | Shepherd et al. | 260/397.2 |
| 2,813,879 | 11/1957 | Wildi et al. | 260/397.2 |
| 2,838,526 | 6/1958 | Laubach | 260/397.2 |
| 2,840,574 | 6/1958 | Chemerda et al. | 260/397.2 |
| 2,979,440 | 4/1961 | Smythe | 195/64 |
| 3,859,437 | 1/1975 | Weigand | 424/238 |
| 3,959,540 | 5/1976 | Leiberich et al. | 428/35 |
| 4,001,480 | 1/1977 | Shank | 428/411 |
| 4,009,076 | 2/1977 | Green et al. | 195/63 |
| 4,079,125 | 3/1978 | Sipos | 424/32 |
| 4,106,991 | 8/1978 | Markussen et al. | 195/63 |
| 4,251,387 | 2/1981 | Lim et al. | 252/316 |
| 4,348,384 | 9/1982 | Horikoshi et al. | 424/101 |
| 4,362,711 | 12/1982 | Cerami | 424/33 |
| 4,482,630 | 11/1984 | Allen et al. | 435/187 |
| 4,492,706 | 1/1985 | Kallai-Sanfacon | 424/270 |
| 4,603,142 | 7/1986 | Burger et al. | 514/456 |
| 4,689,326 | 8/1987 | Hall et al. | 514/217 |

FOREIGN PATENT DOCUMENTS 59-186972  10/1984  Japan .

OTHER PUBLICATIONS

Allen W. Brinkley, Andrew R. Gottesman, and Glen E. Mott, Department Of Pathology, The University of Texas Health Science Center at San Antonio, San Antonio, Texas, Isolation and Characterization of New Strains of Cholosterol–Reducing Bacteria from Baboons, Applied and Environmental Microbiology, Jan. 1982, vol. 43, No. 1, pp. 86–89.

Lehninger, "Biochemistry", Second Edition, Worth Publishers, Inc., (1975), p. 685.

Guyton, "Testbook of Medical Physiology", Fifth Edition, W.B. Saunders Company, (1976), pp. 924 & 925.

Eyssen, "Biohydrogenation of Sterols and Fatty Acids by the Intestinal Microflora", *The American Journal of Clinical Nutrition*, vol. 27: Nov. 1974, pp. 1329–1340.

Brinkley et al. "Applied and Environmental, Microbiology," pp. 1130–1132, Dec. 1980.

*Primary Examiner*—Lien Tran
*Attorney, Agent, or Firm*—Zarley, McKee, Thomte, Voorhees & Sease

[57] ABSTRACT

A method of decreasing plasma cholesterol is disclosed. The method includes oral administration of coprostanol-producing bacteria to humans. These organisms, once in the small intestine, will reduce free cholesterol to coprostanol, which is absorbed poorly. Pharmaceutical compositions for delivery are included as are different methods of delivery such as placing the microorganisms in food.

11 Claims, 1 Drawing Sheet

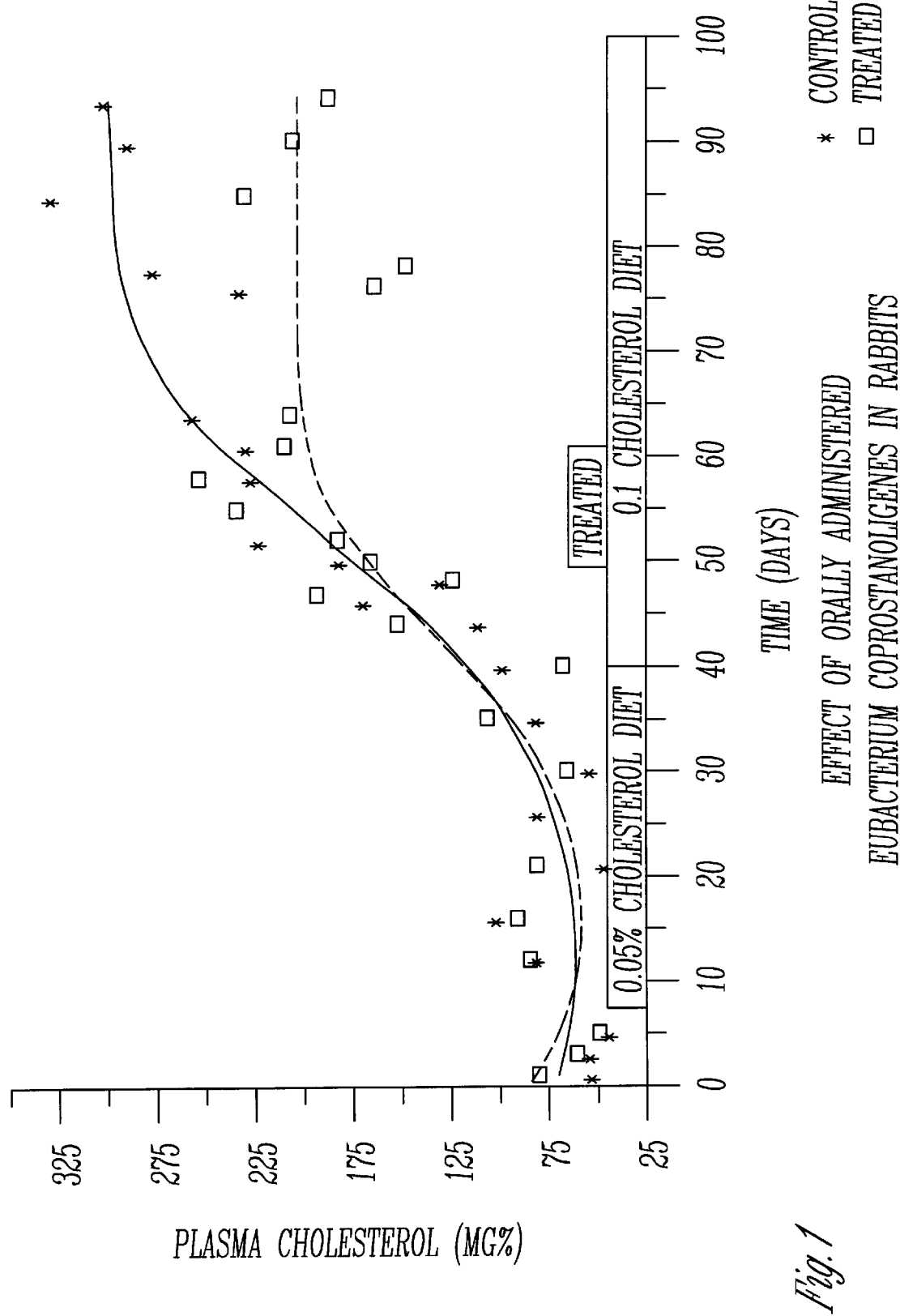

ORAL ADMINISTRATION OF COPROSTANOL PRODUCING MICROORGANISMS TO HUMANS TO DECREASE PLASMA CHOLESTEROL CONCENTRATION

CROSS REFERENCE TO RELATED APPLICATION

This is a continuation of application Ser. No. 07/970,565 filed on Nov. 3, 1992 now abandoned and a continuation-in-part of commonly assigned application Ser. No. 07/796,403 filed Nov. 22, 1991 now U.S. Pat. No. 5,436,004, which is itself a continuation-in-part of Ser. No. 07/339,229, filed Apr. 17, 1989 now abandoned, which is itself a continuation-in-part of Ser. No. 07/222,016 filed Jul. 21, 1988, now U.S. Pat. No. 4,921,710, issued May 1, 1990.

BACKGROUND OF THE INVENTION

Coronary heart disease, atherosclerosis, is the leading cause of human mortality in the United States, as well as in many other developed countries, and is responsible for more deaths than all forms of cancer combined. It is generally recognized that high blood cholesterol concentrations provide a significant risk factor associated with atherosclerosis.

Cholesterol is present in the blood as free and esterified cholesterol within lipoprotein particles, commonly known as chylomicrons, very low density lipoproteins, low density lipoproteins and high density lipoproteins. Concentration of total cholesterol in the blood is influenced by (1) absorption of cholesterol from the digestive tract, (2) synthesis of cholesterol from dietary constituents such as carbohydrates, proteins, fats and ethanol, and (3) removal of cholesterol from blood by tissues, especially the liver, and subsequent conversion of the cholesterol to bile acids, steroid hormones, and biliary cholesterol. The bile acids and cholesterol in bile are secreted into the intestine from which they may be recycled back to the blood or be excreted into the feces. In summation of these physiological processes, the concentration of cholesterol in the blood is controlled by a balance of inputs and outputs. The two inputs are cholesterol absorbed from the diet and cholesterol that is synthesized within the body and secreted into the blood. Typical values of adult humans for absorption are 335 mg daily and for synthesis are 800 mg.

The outputs regulating the concentration of cholesterol in blood include sloughing skin cells (about 85 mg cholesterol daily), excretion of steroid hormones (about 50 mg cholesterol daily), excretion of bile acids in feces (400 mg cholesterol equivalent daily), and excretion of sterols in feces (600 mg cholesterol equivalent daily). The fecal sterols include cholesterol, cholestanol, coprostanol, and plant sterols. The whole body of the adult human contains about 100 grams of cholesterol, most of which is in the nonesterfied form.

Maintenance of blood cholesterol concentrations is influenced by both genetic and environmental factors. Genetic factors include concentration of rate-limiting enzymes in cholesterol biosynthesis, concentration of receptors for low density lipoproteins in the liver, concentration of rate-limiting enzymes for conversion of cholesterols bile acids, rates of synthesis and secretion of lipoproteins and gender of person. Environmental factors influencing the hemostasis of blood cholesterol concentration in humans include dietary composition, incidence of smoking, physical activity, and use of a variety of pharmaceutical agents. Dietary variables include amount and type of fat (saturated and polyunsaturated fatty acids), amount of cholesterol, amount and type of fiber, and perhaps amounts of vitamins such as vitamin C and D and minerals such as calcium.

Pharmaceutical agents in current use that usually cause a hypocholesterolemic response include lovastatin, which decreases cholesterol synthesis in the body, and cholestyramine, which increases bile acid excretion. An increase in bile acid excretion causes the liver of the person to convert more cholesterol to bile acids and to incorporate less cholesterol in very low density and low density lipoproteins for secretion into the blood. Hence, cholestyramine usually causes a hypocholesterolemic response.

Similar to that for bile acid excretion, increases in the excretion of cholesterol and other sterols into the feces usually will cause a hypocholesterolemic response because the liver would partition more cholesterol into the bile and thus less would be available for incorporation into lipoproteins for secretion into the blood. Typically, a human secretes about 1,000 mg of cholesterol from the liver into the bile for entry into the small intestine. This biliary cholesterol then becomes a part of the dietary cholesterol pool in the small intestine and thus may be absorbed to maintain cholesterol homeostasis.

The present invention discloses a method and means for decreasing the amount of biliary and dietary cholesterol that is absorbed by the small intestine through oral administration of coprostanol-producing microorganisms. Several species of bacteria including *Eubacterium coprostanoligenes* (previously called Eubacterium sp. strain HL by us) isolated in pure culture from an Iowa State University hog lagoon (ATCC No. 21408) contain the enzyme cholesterol reductase. These bacteria, which produce this enzyme, are capable of converting cholesterol to coprostanol. The resultant coprostanol product is absorbed poorly by humans and, instead of being absorbed through the intestine into the blood, will be passed through the intestine and excreted in the feces of the human.

Thus, an objective of the present invention is to decrease cholesterol absorption in the small intestine through administration of coprostanol-producing microorganisms.

Another object of the invention is to convert cholesterol present in the small intestine to coprostanol, which will be excreted.

Yet another objective of the invention is to lower plasma concentration of cholesterol in humans by generating a hypocholesterolemic response resulting in partitioning by the liver of more cholesterol into bile with less available for incorporation into lipoproteins for secretion into the blood.

Another objective of the present invention is to provide a pharmaceutical composition for oral administration, which will release the coprostanol-producing organisms in the small intestine of humans.

The method and means of accomplishing each of the above objectives as well as others will become apparent from the detailed description of the invention that follows hereinafter.

BRIEF DESCRIPTION OF THE DRAWINGS

FIG. 1 is a graph showing a decrease in plasma cholesterol concentration for rabbits treated with orally administered *Eubacterium coprostanoligenes*.

SUMMARY OF THE INVENTION

This invention relates to the oral administration of coprostanol-producing microorganisms as a means of decreasing cholesterol concentrations in the blood of humans. These microorganisms will decrease blood cholesterol concentrations by converting biliary and dietary cholesterol, which normally would be absorbed through the small intestine, to nonabsorbable coprostanol, which then is excreted. The invention also comprises a pharmaceutical composition for administration of the microorganisms. Preferably the microorganisms are encapsulated in a dose delivery system that decreases the probability of release of the organisms in the human stomach but increases the probability of release in the proximal small intestine. The microorganisms also may be administered as a constituent of foods, such as milk, meats, and yogurt.

DETAILED DESCRIPTION OF THE INVENTION

*Eubacterium coprostanoligenes* has been deposited at the American Type Culture Collection, 10801 University Boulevard Manassas, Va. 20110-2209, USA on Feb. 10, 1993. The deposit strain has been assigned Accession No. 51,222. The culture deposited with the ATCC is taken from the same cultures maintained by Iowa State University, Department of Animal Science, Ames, Iowa 50011, since prior to the filing date of this application. This culture at Iowa State University has been maintained under conditions which assure access to the cultures will be available during the pendency of this patent application to those determined by the Commissioner of Patents and Trademarks to be entitled thereto under 37 C.F.R. § 1.14 and 35 U.S.C. § 122.

The deposits are available as required by foreign patent laws in countries wherein counterparts of the subject application or its progeny, are filed. However, it should be understood that applicant granting of permission to the depository to distribute samples of the deposit does not constitute an expressed or implied license to practice the invention claimed in any patent issuing on the subject application or any other patent.

The subject cultured deposits will be stored and made available to the public in accordance with the provisions of the Budapest Treaty for the deposit of microorganisms, i.e., they will be stored with all the care necessary to keep them viable and uncontaminated for a period of at least five years after the most recent request for the furnishing of a sample of the deposits, and in any case, for a period of at least thirty (30) years after the date of deposit or for the enforcable life of any patent which may issue disclosing the cultures. The depositor acknowledges the duty to replace the deposit should the depository be unable to furnish a sample when requested, due to the condition of the deposits. All restrictions on the availability to the public of the subject culture deposits will be irrevocably removed upon the granting of a patent disclosing them.

The mechanism of the enzyme cholesterol reductase and its presence in *Eubacterium coprostanoligenes* species and in several green plants has already been well described and documented in several of my earlier patent applications, of which this is a continuation in part. U.S. Pat. No. 4,921,710 comprises a method of converting cholesterol in food to coprostanol by addition of cholesterol reductase to foods and by injection of the enzyme prior to slaughter for meat animals. In addition, there is a continuation-in-part application now in prosecution for oral administration of the cholesterol reductase enzyme to humans to reduce endogenous and dietary cholesterol. There is also now a pending application that proposes to insert the cholesterol reductase producing gene sequence into meat-producing animals so that it can be "turned on" to decrease cholesterol concentrations. These applications and patents are all incorporated herein by reference.

As described in earlier applications, coprostanol, which is absorbed poorly by humans, is the product representing cholesterol that has been hydrogenated. This reaction is enhanced by the enzymatic activity of cholesterol reductase. This enzyme is present in *Eubacterium coprostanoligenes* isolated from a hog lagoon at Iowa State University. Several other Eubacteria, such as *Eubacterium coprostanoligenes* ATCC 21408, also contain the ability to produce the enzyme and thereby reduce cholesterol to coprostanol. The present application represents yet another extension in clinical and industrial use of cholesterol reductase and involves direct ingestion of the bacteria that contain cholesterol reductase into the small intestine of the humans, allowing the microorganism to convert cholesterol present in the small intestine to coprostanol, which is then excreted rather than absorbed.

The human digestive tract receives dietary cholesterol and liver-derived endogenous cholesterol via secretion of bile into the upper part of the small intestine. In addition, cells sloughed from the digestive tract contribute cholesterol that becomes available for absorption into the intestinal mucosal cells. Typically, diet (about 700 mg per day), sloughed cells (about 400 mg per day), and bile (about 1000 mg per day) contribute more than 2000 mg of cholesterol daily for absorption. The majority of this cholesterol is present as free cholesterol because that is the major form of cholesterol in food, slough cells and bile. Pancreatic cholesterol esterase will catalyze conversion of any cholesteryl esters in the intestinal lumen to free cholesterol and free fatty acids.

Enrichment of contents of the small intestine with one or more species of coprostanol-producing bacteria will cause conversion of cholesterol in the intestinal contents to coprostanol, which is absorbed poorly. Some of the bacteria may become attached to the intestinal mucosal cells and thus carry coprostanol synthesis at or near the site of cholesterol absorption. The enrichment of the small intestinal contents, especially the upper part where significant cholesterol absorption occurs, will decrease markedly the efficiency of absorption of both dietary and endogenous cholesterol, and thus the liver of the human recipient will partition a greater percentage of its cholesterol toward the small intestine via the bile and less toward the blood. This partitioning change will occur because less biliary and dietary cholesterol is transferred to the liver due to cholesterol conversion to the coprostanol in the intestinal lumen.

Pharmaceutical compositions for the introduction of these coprostanol-producing bacteria into the small intestine include bacteria that have been lyophilyzed or frozen in liquid or paste form and encapsulated in a gel capsule. The gel cap material must be a specific polymeric material to form a delivery pill or capsule that is resistant to degradation by the gastric acidity and pepsin of the stomach but is degraded with concomitant release of bacteria by the higher pH and bile acid contents in the proximal small intestine. The released and now active bacteria then would catalyze conversion of cholesterol present in the small intestine to coprostanol. Pharmaceutical carriers also could be combined with the bacteria. These would include saline-phosphate buffer for a solution that may be directly administered to the person.

Another method of administration of these microorganisms to the small intestine would include adding the coprostanol-producing bacteria directly to food sources. Foods, such as yogurt or milk, may be supplemented with coprostanol-producing organisms without affecting their taste or appearance. Upon ingestion, when the food products are being digested and absorbed by the small intestine, the microorganisms will convert cholesterol present in the small intestine to coprostanol, preventing absorption of the cholesterol into the blood stream.

EXAMPLE 1

The ability of orally administered coprostanol-producing bacteria to decrease serum blood cholesterol concentrations is demonstrated by the following example.

Six adult New Zealand White rabbits were assigned randomly to two groups of three rabbits each. Treated rabbits received 4 ml of *Eubacterium coprostanoligenes* suspension (~2×10$^7$ cells/ml). Control rabbits received the same dose of a boiled (dead) *Eubacterium coprostanoligenes*. The strain of bacteria that we used was a coprostanol-producing *Eubacterium coprostanoligenes* sp. that was isolated in pure culture from an Iowa State University hog lagoon. Eubacterium sp. strain HL (hog lagoon), now called *Eubacterium coprostanoligenes*, is described in a doctoral dissertation written by Timothy A. Freier during 1991 and is available in the Iowa State University Library. The bacterial preparations were administered via a tube placed into the esophagus once daily for 10 days beginning on day 50 and concluding on day 59. On day 1 of the experimental period, cholesterol was added to the diet at a concentration of 0.05% of air-dry weight of the feed to cause hypercholes-terolemia. On day 38, the cholesterol concentration of the diet was increased to 0.10%. This diet was fed to the rabbits through day 94.

The effects of oral administration of the *Eubacterium coprostanoligenes* suspension on plasma cholesterol concentrations are shown in FIG. 1. The plasma cholesterol concentration was elevated from about 75 mg % to about 225 mg % by the supplemental dietary cholesterol. The effect of bacteria was not observed until after 8 days of administration of the bacteria, but the hypocholesterolemic effect was still observed 33 days after the rabbits were no longer fed the bacteria. From day 64 through day 94, plasma cholesterol concentration of treated rabbits (189 mg %) was significantly lower (P<0.001) than that of controls (276 mg %). When intestinal contents of control and treated rabbits were assayed for the presence of Eubacteria, the treated rabbits had maintained significantly greater numbers of the coprostanol-producing bacteria in the contents of the cecum and large intestine. Maintenance of *Eubacterium coprostanoligenes* in the treated rabbits occurred because of (1) attachment of *Eubacterium coprostanoligenes* to the intestinal and cecal epithelia and/or (2) recycling of the *Eubacterium coprostanoligenes* through the digestive tract via coprophagy. The treated rabbits had significantly greater amount of coprostanol in their fecal samples than did the control rabbits. Furthermore, administration of the *Eubacterium coprostanoligenes* had no adverse effects on consistency of the feces or on health of the rabbits.

In conclusion, these data clearly indicate that oral administration of a coprostanol-producing bacterium caused significant hypocholesterolemic effects in rabbits. Similar effects would be expected in humans because of the many similarities in nutrition, physiology, and biochemistry of rabbits and humans.

EXAMPLE 2

Prophetic

Foods that are about to be ingested could be supplemented with coprostanol-producing microorganisms. Coprostanol-producing *Eubacterium coprostanoligenes* would be grown in media and separated from the media in a paste form by centrifugation. Traditional yogurt cultures obtained from any commercial dairy could be mixed with the *Eubacterium coprostanoligenes* culture. This mixture of cultures then could be added to the basic dairy yogurt premix without affecting taste or consistency. The yogurt then would be produced and packaged by using traditional commercial procedures. In another example, the *Eubacterium coprostanoligenes* could be added to already produced yogurts.

Another example would be to add the *Eubacterium coprostanoligenes* to milk after it has been homogenized and sterilized. Such a method is currently used for adding the *Lactobacillus acidophilus* organisms to milk by the dairy industry. These commercial procedures likely could be used with coprostanol-producing Eubacterium with similar results. Any food source containing bacteria could likely be used by supplementing with coprostanol producing bacteria, such as cheese or meat products that have selected microorganisms added during processing.

Once these food products have been prepared to contain the coprostanol-producing organisms, they may be ingested. Once in the small intestine, the *Eubacterium coprostanoligenes* will perform the familiar reduction of cholesterol to coprostanol.

What is claimed is:

1. A method of decreasing blood cholesterol concentration in hypercholesterolemic mammals, said method comprising:

(a) orally administering cholesterol reducing effective amount of *Eubacterium coprostonaligenes* microorganism into the small intestine of said mammal.

2. The method of claim 1 wherein said mammal is a human.

3. The method of claim 1 wherein absorption of dietary and endogenous cholesterol is decreased due to reduction of cholesterol to coprostanol by said microorganism.

4. The method of claim 3 wherein said coprostanol is not absorbed by the small intestine but is instead expelled in the feces of said mammal.

5. A pharmaceutical composition for use in reduction of blood cholesterol concentration in humans, said composition comprising:

*Eubacterium coprostanoligenes* microorganism having ATCC Accession No. 51,222 and a pharmaceutically acceptable carrier.

6. The pharmaceutical composition of claim 5 wherein said microorganism is in a cholesterol-reducing effective unit dosage form.

7. The pharmaceutical composition of claim 5 wherein said pharmaceutically acceptable carrier is saline-phosphate buffer solution.

8. The pharmaceutical composition of claim 5 wherein said pharmaceutical carrier is a material useful for introducing said composition that is medically acceptable and does not interfere with the cholesterol-reducing properties of said microorganism.

9. The composition of claim 5 wherein said composition is encapsulated in a pill or capsule that is resistant to degradation by gastric acidity and pepsin, but is degraded with concomitant release of said *Eubacterium coprostanoligenes* microorganism by higher pH and bile acids present in the proximal small intestine.

10. The composition of claim 9 wherein said *Eubacterium coprostanoligenes* microorganisms are freeze dried.

11. A method of decreasing blood cholesterol concentration in rabbits, said method comprising:

(a) orally administering a cholesterol reducing effective amount of *Eubacterium coprostanoligenes* into the small intestine of a rabbit;

(b) decreasing absorption of dietary and endogenous cholesterol, through conversion of said cholesterol to coprostanol by said microorganism.

* * * * *